(12) United States Patent
Platzek et al.

(10) Patent No.: US 7,189,879 B2
(45) Date of Patent: Mar. 13, 2007

(54) PROCESS FOR THE PRODUCTION OF 1-HYDROXYMETHYL-1,3,5-TRIAZAPENTANE, TRIHYDROCHLORIDE

(75) Inventors: Johannes Platzek, Berlin (DE); Jan Huebner, Berlin (DE); Orlin Petrov, Berlin (DE)

(73) Assignee: Schering AG, Berlin (DE)

( * ) Notice: Subject to any disclaimer, the term of this patent is extended or adjusted under 35 U.S.C. 154(b) by 16 days.

(21) Appl. No.: 11/135,647

(22) Filed: May 24, 2005

(65) Prior Publication Data

US 2006/0014983 A1    Jan. 19, 2006

Related U.S. Application Data

(60) Provisional application No. 60/575,838, filed on Jun. 2, 2004.

(30) Foreign Application Priority Data

May 24, 2004  (DE) ................. 10 2004 026 102.4

(51) Int. Cl.
*C07C 209/60* (2006.01)
*C07C 271/16* (2006.01)
*C07C 549/419* (2006.01)

(52) U.S. Cl. .................. 564/474; 564/475; 564/487; 560/159; 549/419

(58) Field of Classification Search .................. None
See application file for complete search history.

(56) References Cited

U.S. PATENT DOCUMENTS 6,676,929 B2    1/2004  McMurry et al.
2002/0164289 A1   11/2002  McMurry et al.

FOREIGN PATENT DOCUMENTS

DE        3728525 A1      3/1989
DE        3806795 A1      9/1989
WO     WO 96/23526 A2     8/1996

OTHER PUBLICATIONS

Sajiki, Hironao, et al: "Synthesis of Enantiomerically Pure 1-(R)- And 1-(S)-Hydroxymethyl-DTPA Penta-T-Butyl Esters Via Chiral Amino Alcohols" Synthetic Communications (1996) 26(13), 2511-2522 Coden: Syncav; ISSN: 0039-7911, XP009051769.

Amedio, et al. A Practical Manufacturing Synthesis of 1-(R)-Hydroxymethyl-DTPA: An Important Intermediate in the Synthesis of MRI Contrast Agents, Synthetic Communications, 29(14), pp. 2377-2391; 1999.

*Primary Examiner*—Brian Davis
(74) *Attorney, Agent, or Firm*—Millen, White, Zelano, Branigan, P.C.

(57) ABSTRACT

A new process for the production of 1-hydroxymethyl-1,3,5-triazapentane, trihydrochloride is described.

21 Claims, No Drawings

PROCESS FOR THE PRODUCTION OF 1-HYDROXYMETHYL-1,3,5-TRIAZAPENTANE, TRIHYDROCHLORIDE

This application claims the benefit of the filing date of U.S. Provisional Application Ser. No. 60/575,838 filed Jun. 2, 2004 which is incorporated by reference herein.

The invention relates to the subject that is characterized in the claims, i.e., a new process for the production of 1-hydroxymethyl-1,3,5-triazapentane, trihydrochloride.

The use of contrast media for visualizing the intravascular space (blood-pool imaging) is one of the important applications in MRI angiography. In this connection, a compound, the so-called MS-325 (U.S. Pat. No. 6,676,929 and WO 96/23526), which already successfully completed phase III clinical testing and has been filed with the FDA for approval, has proven its value especially well. The synthesis of MS-325 is described in Synthetic Communications, 26(13), 2511–2522 (1996) and Synthetic Communications, 29(14), 2377–2391 (1999).

Within the scope of the development of this compound, it was desired to provide larger amounts of substance. Since the substance is administered to humans, strict standards on the purity of the final product as well as on the intermediate products must be set. Based on the large range of applications to be expected, such a high-grade product should also be producible at a representative cost (in terms of price). There is therefore a desire to have as economically advantageous a synthesis as possible. A very important intermediate product of the synthesis of MS-325 is the 1-hydroxymethyl-1,3,5-triazapentane, trihydrochloride. (I)

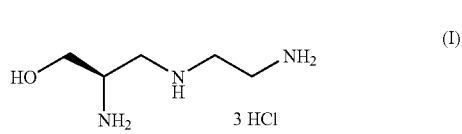

In addition to the synthesis that is described in U.S. Pat. No. 6,676,929 and WO 96/23526, 2 synthesis methods are described in detail:

1$^{st}$ Method (Synthetic Communications, 26(13), 2511–2522 (1996))

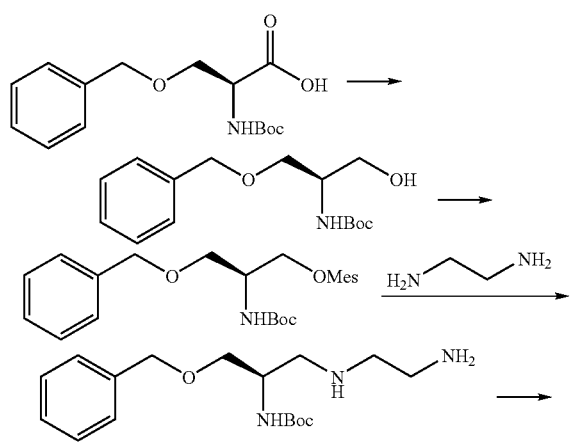

The total yield of the synthesis is: 54.2% of theory.

The very costly starting material O-benzyl-Boc-serine, which is obtained by a very loss-prone alkylation of the Boc-serine and is difficult to clean, is disadvantageous in this synthesis (probably a research synthesis on a laboratory scale). The production of the primary alcohol from the acid is performed via a mixed anhydride formation by in-situ reduction with sodium borohydride. Specifically when scaling such reactions up to the 100 kg scale, problems can be expected, since extended addition times and exothermal reactions cause the anhydride to decompose. In addition, the use of larger amounts of trifluoroacetic acid, which is used in the cleavage of the BOC group, is not optimal not only for reasons of cost but also for aspects of environmental politics. In addition, the synthesis contains a chromatographic purification, which, out of concern for the operational process, is to be avoided as much as possible.

2$^{nd}$ Method (Synthetic Communications, 29(14), 2377–2391 (1999)

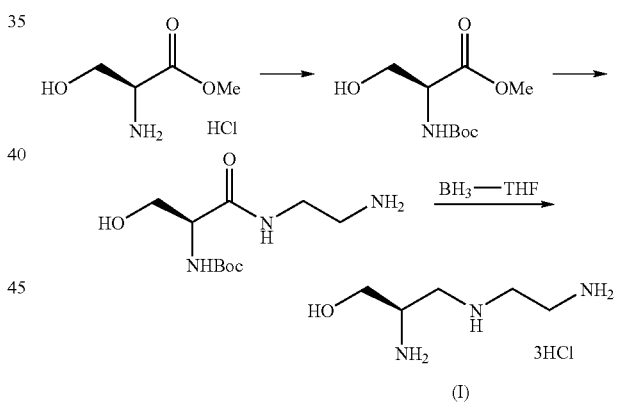

The total yield of the synthesis is: 57.9% of theory.

A great drawback of this synthesis is the use of the very costly borane-THF complex (Aldrich 2003/2004: 20 liters of 1.0 M borane-tetrahydrofuran complex 2403.10 EURO!), which is used in 3× excess (!). In addition, a heavy dilution, which hinders up-scaling, of about 16×THF relative to the charging material is noteworthy. The handling of diborane on an industrial scale (1000-8000 l stirrer) is in any case problematical and of concern with respect to safety. Fatal incidents in handling large amounts of diborane solution have already been reported (Pfizer). In addition, the boric acid that accumulates with the working-up is to be filtered off, which is very difficult as far as processing is concerned.

To produce larger amounts of MS-325 (i.e., production of several thousand kilograms of product after introduction on the market), there is a great need to develop as economical a synthesis as possible for the 1-hydroxymethyl-1,3,5-triazapentane, trihydrochloride, (1).

This process satisfies the set requirements to a large extent.

The compound of formula I

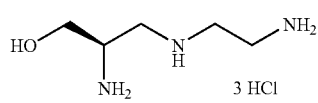

(I)

is produced by cleavage of the Z protective group or the Boc-protective group from compounds of formula IIa or IIb

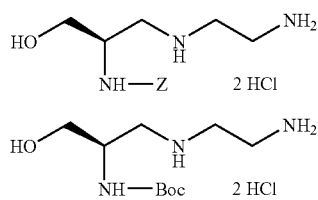

(IIa)

(IIb)

The cleavage is carried out according to the methods of protective group cleavage for amines that are known to one skilled in the art and subsequent conversion into the hydrochlorides. The cleavage of the Z and Boc group is described in T. W. Green, *Protective Groups in Organic Synthesis*, John Wiley & Sons, N.Y., 1981 and in P. J. Kocienski, *Protecting Groups*, Georg Thieme Verlag Stuttgart, 1994.

In the case of the BOC protective group, the cleavage of the BOC group is carried out by treatment with aqueous hydrochloric acid (5% up to concentrated HCl), at temperatures of 0 to 100° C., preferably 20–80° C. The trihydrochloride can be precipitated by adding an alcohol, such as, e.g., ethanol, methanol, isopropanol, n-butanol, isobutanol or mixtures of these alcohols, or mixtures of these alcohols with THF, methyl-tert-methyl ether or acetone and can be isolated in crystalline form. In many cases, it has proven advantageous to concentrate by evaporation the aqueous hydrochloric acid solution before the organic solvent is added.

In the case of the Z protective group, the cleavage of the Z group is carried out by treatment with aqueous hydrochloric acid (10% up to concentrated HCl), at temperatures of 0 to 100° C., preferably 60–100° C., or by catalytic hydrogenation on Pd/C in aqueous solution. Mixtures of water with ethanol, methanol or THF can also be used optionally with the addition of aqueous hydrochloric acid for hydrogenation. The hydrogenation is carried out at 10–60° C., preferably at room temperature, at pressures of 2–10 bar. After the catalyst is filtered off, the product-containing filtrate is worked up.

The trihydrochloride (I) can be precipitated by adding an alcohol, such as, e.g., ethanol, methanol, isopropanol, butanol, isobutanol or mixtures of these alcohols, preferably an ethanol/butanol mixture, or mixtures of these alcohols with THF, methyl-tert-butyl methyl ether or acetone and can be isolated in crystalline form. In many cases, it has proven advantageous to concentrate by evaporation the aqueous hydrochloric acid solution (even after hydrogenation) before adding the organic solvent.

The trihydrochloride (I) is dried in a vacuum (T=25–50° C./6–48 hours) and then obtained as a colorless, crystalline powder.

Of course, the hydrobromides, or, with sulfuric acid, the sulfates or hydrosulfates, etc., can also be produced by use of HBr instead of HCl.

Compounds of formulas IIa and IIb are obtained from compounds of general formulas IIIa and IIIb

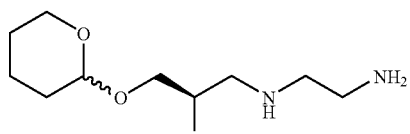

(IIIa)

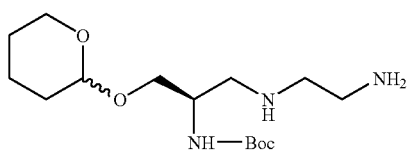

(IIIb)

by cleavage of the THP protective group. The cleavage is carried out according to the methods of cleavage of THP-ether that are known to one skilled in the art; T. W. Green, *Protective Groups in Organic Synthesis*, John Wiley & Sons N.Y., 1981 and in P. J. Kocienski, *Protecting Groups*, Georg Thieme Verlag Stuttgart, 1994. Gupta, Priti; Fernandes, Rodney A.; Kumar, Pradeep; Tetrahedron Lett.; 44; 22; 2003; 4231–4232. Burton, T. S. et al.; J.Chem.Soc.Perkin Trans.1; 1976; 2550–2556; Evans, R. J. D. et al.; J.Chem.Soc.Perkin Trans.1; 1974; 552–556.

The cleavage of the THP group is carried out in the way that the compounds of formulas IIIa and IIIb are dissolved in an alcohol, such as, e.g., ethanol, methanol, isopropanol, isobutanol or mixtures of these alcohols, or mixtures of these alcohols with water, THF, methyl-tert-butyl methyl ether or acetone, and a mineral acid, such as HCl, sulfuric acid, phosphoric acid, but preferably aqueous hydrochloric acid (10% up to concentrated HCl, preferably concentrated) is added and stirred at temperatures of 0–80° C., preferably 0 –50° C. The reaction time is 30 minutes to 12 hours, preferably 3 to 6 hours. The product precipitates during the reaction. To increase the yield, optionally THF, methyl-tert-butyl methyl ether or acetone can ultimately be added for complete crystallization.

The dihydrochlorides (IIa and IIb) are dried in a vacuum (T: 25–50° C./6–48 hours) and then obtained as colorless, crystalline powder.

Compounds of formulas IIa and IIIb are obtained from compounds of formulas IVa and IVb

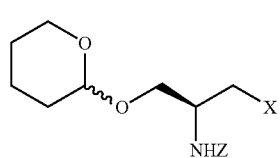

(IVa)

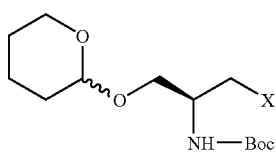

(IVa)

in which X stands for a tosyloxy or a mesyloxy group by reaction with 1,2-diaminoethane.

The reaction is carried out at temperatures of 10 to 70° C., preferably 30–60° C. The reaction time is 3 to 12 hours, preferably 3–8 hours. The reaction can be performed either directly in pure diaminoethane, or by adding a solvent such as THF, dioxane, 2-methyl-THF, pyridine or alcohols, such as ethanol, methanol, isopropanol, or butanol. 10 to 40 molar equivalents, preferably 12 to 25 molar equivalents, of diaminoethane relative to IVa or IVb can be used.

For working-up, excess diaminoethane optionally can be distilled off in a vacuum, or, after adding water, the product can be extracted with suitable solvents, such as, e.g., THF, ethyl acetate, butanol, dichloromethane, or 2-methyl-THF.

The alkylation of diamines is described in, e.g.: Palmer, Brian D.; Lee, Ho H.; Johnson, Paul; Baguley, Bruce C.; Wickham, Geoffrey; et al.; J. Med. Chem.; 33; 11; 1990; 3008–3014.

Gibson, Dan; Gean, Keria-Fiorella; Ben-Shoshan, Raphael; Ramu, Avner; Ringel, Israel; Katzhendler, Jehoshua; J.Med.Chem.; 34; 1; 1991; 414–420.

Lee, Ho H.; Palmer, Brian D.; Baguley, Bruce C.; Chin, Michael; McFadyen, W. David; et al.; J.Med.Chem.; 35; 16; 1992; 2983–2987.

Skarzewski, Jacek; Daniluk, Ewa; Monatsh.Chem.; 114; 1983; 1071–1078. Sajiki, Hironao; Ong, Karen Y.; Nadler, Samuel T.; Wages, Heather E.; McMurry, Thomas J.; Synth.Commun.; 26; 13; 1996; 2511–2522.

EP 680467 (Schering AG).

In some cases, it has proven especially advantageous to produce the compound of formula I from compounds of formulas IIIa and IIIb by cleavage of THP and N protective group groups in a single-pot reaction.

In this connection, the cleavage of both protective groups is carried out by treatment with aqueous hydrochloric acid (5% to concentrated HCl) at temperatures of 0 to 100° C., preferably 20–95° C. The trihydrochloride can be precipitated by adding an alcohol, such as, e.g., ethanol, methanol, isopropanol, n-butanol, isobutanol or mixtures of these alcohols, or mixtures of these alcohols with THF, methyl-tert-butyl methyl ether or acetone and isolated in crystalline form. In many cases, it has proven advantageous to concentrate by evaporation the aqueous hydrochloric acid solution before the organic solvent is added.

Compounds of formulas IVa and IVb are obtained according to the methods, known to one skilled in the art, of mesylation or tosylation of the alcohols of general formulas Va and Vb

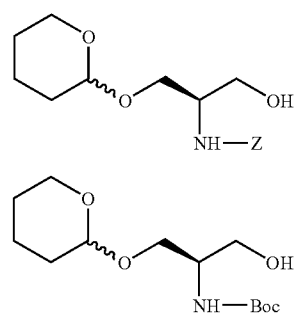

The reaction of alcohols Va or Vb is carried out with 1–1.5 equivalents of methane-sulfonic acid chloride or p-toluene-sulfonic acid chloride in aprotic solvents, such as THF, 2-methyl-THF, dichloromethane, toluene, preferably THF with the addition of an amine, such as, e.g., triethylamine, Hünig base or pyridine, preferably triethylamine, at temperatures of −20° C. to +20° C., preferably −5 to +10° C. The reaction time is 1–12 hours, preferably 1–3 hours.

LITERATURE

Fukushi, Hideto; Mabuchi, Hiroshi; Terashita, Zen-ichi; Nishikawa, Kohei; Sugihara, Hirosada; Chem.Pharm.Bull.; 42; 3; 1994; 551–559.

Higashiura, Kunihiko; Morino, Hiroe; Matsuura, Hirohide; Toyomaki, Yoshio; Ienaga, Kazuharu; J.Chem.Soc.Perkin Trans.1; 1989; 1479–1481.

Donner, B. G.; Tetrahedron Lett.; 36; 8; 1995; 1223–1226.

Sajiki, Hironao; Ong, Karen Y.; Nadler, Samuel T.; Wages, Heather E.; McMurry, Thomas J.; Synth.Commun.; 26; 13; 1996; 2511–2522.

Journal; Sajiki, Hironao; Ong, Karen Y.; Nadler, Samuel T.; Wages, Heather E.; McMurry, Thomas J.; Synth.Commun.; 26; 13; 1996; 2511–2522.

Benoist, Eric; Loussouam, Anthony; Remaud, Patricia; Chatal, Jean-Francois; Gestin, Jean-Francois; Synthesis; 8; 1998; 1113–1118.

The compound IVb with X=p-toluenesulfoxy is known in the literature: Sasaki, N. Andre; Hashimoto, Chiyomi; Potier, Pierre; Tetrahedron Lett.; 28; 48; 1987; 6069–6072.

The compound Va is also known in the literature: Wang, Yi-Fong; Lalonde, James J.; Momongan, Milagros; Bergbreiter, David E.; Wong, Chi-Huey; J.Amer.Chem.Soc.; 110; 21; 1988; 7200–7205.

The analogous BOC compound Vb is described in: Sasaki, N. Andre; Hashimoto, Chiyomi; Potier, Pierre; Tetrahedron Lett.; 28; 48; 1987; 6069–6072.

The use of mesylates IVa and IVb is preferred.

Compounds of general formula V are known in the literature.

The advantages of the new process are:
1. Higher total yield compared to the prior art (see below)
2. Simple procedure (no intermediate purification of the precursors)
3. Reasonably-priced starting materials
4. Crystalline intermediate compounds that make purification possible (important from the regulatory standpoint)
5. Avoidance of DIBORANE (price/safety)
6. Avoidance of trifluoroacetic acid Based on the simplified procedure, it is made possible to easily and unproblematically produce batches on the multi-kg scale. The following two diagrams are used to illustrate the new process:
1. Z Process (Two-Pot)
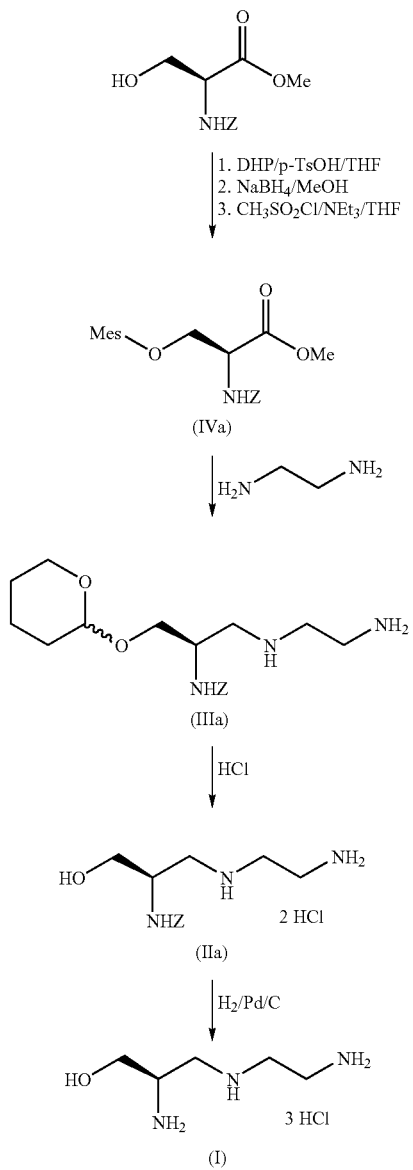
Total yield: 75% of theory
2. Z Process (Single-Pot)
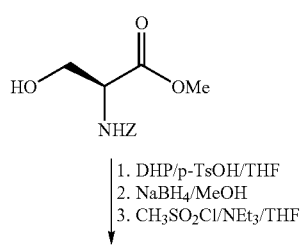
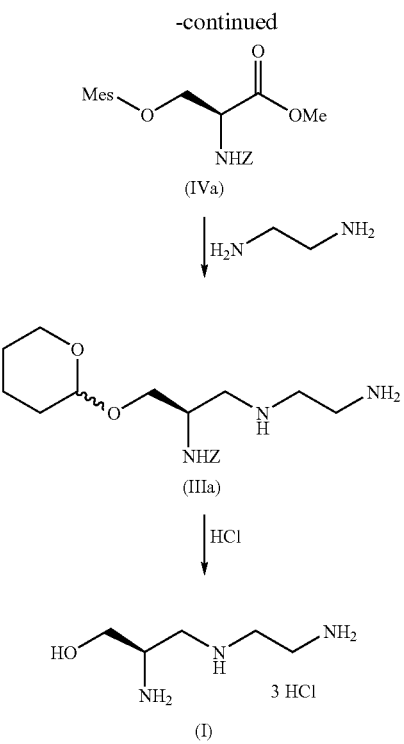
Total yield: 73% of theory
3. Boc Process (Two-Pot)
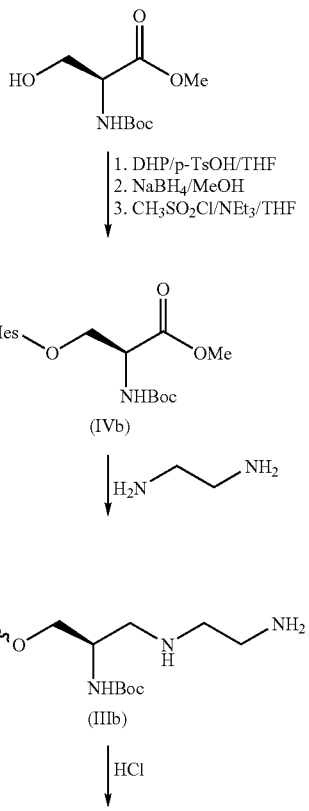

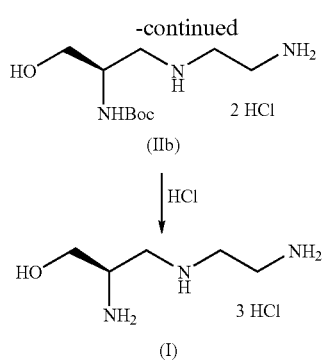

Total yield: 71% of theory

4. Boc Process (Single-Pot)

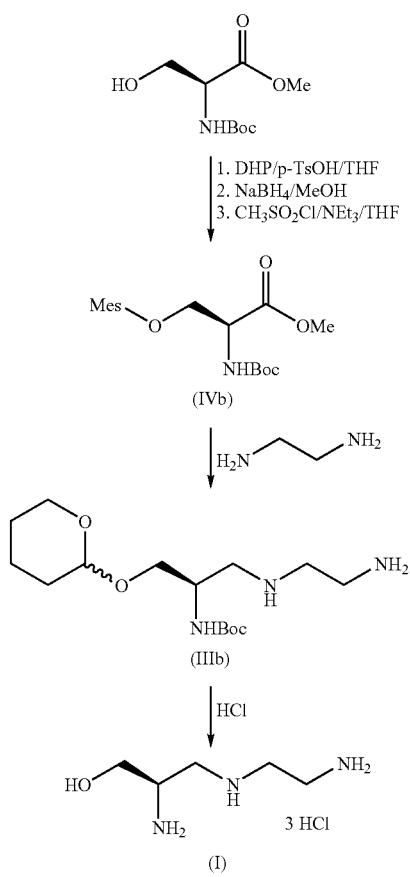

Total yield: 72% of theory

Although the one-pot processes are shorter, the two-pot processes are preferred for regulatory reasons, since they make possible an additional possibility of purification of intermediate compounds IIa or IIb.

The Z process is preferably used.

The total yields of the Z process and the Boc process are significantly higher in both cases than the process that is described in the literature. The simple implementation of these processes allows batches on the scale of up to 8000 l to be produced. In addition, the production costs, because of the higher total yield and the simpler performance of the process, have been significantly reduced.

The synthesis also allows the production of corresponding antipodes or else the racemate of target compound (I).

The examples below are used to explain the subject of the invention.

EXAMPLES

Example 1

Z Method/Two-Pot Process 1 a) 3-Aza-5-amino-1-(R)-hydroxymethyl-1-(benzyloxycarbonylamino)pentane, dihydrochloride 500 g (1974.2 mmol) of (S)-Z-serine methyl ester is introduced into 2000 ml of tetrahydrofuran (THF) and 199.3 g (2369 mmol) of dihydropyran, and 100 mg of p-toluenesulfonic acid is added. It is heated for 6 hours at 60° C. After the reaction is completed, 1000 ml of solvent is distilled off (removal of excess dihydropyran).

2000 ml of fresh THF is added, and 227 g (6.00 mol) of sodium borohydride is added, and it is cooled to 0° C. 2500 ml of methanol is slowly added in drops to this suspension, and the temperature is kept between 2° C. and 6° C. (gas generation). After the addition is completed, it is stirred for 3 more hours at 10° C. 4000 ml of water is added, and the organic solvent is distilled off to a large extent in a vacuum. Then, it is extracted two times with 2000 ml of ethyl acetate in each case. The combined ethyl acetate phases are largely concentrated by evaporation in a vacuum, and the remaining oil is taken up in 3000 ml of THF.

405 g ( 4.00 mol) of triethylamine is added, and it is cooled to −5° C. Then, 248.7 g (2.17 mol) of methanesulfonic acid chloride is added in drops, and the temperature is kept between −5° C. to 0° C. After the addition is completed, it is stirred for one more hour at 0° C.

In the thus obtained solution, 1923 g (32 mol) of 1,2-diaminoethane is quickly added and stirred for 5 hours at 50° C. 6000 ml of water, as well as 176 g (4.4 mol) of sodium hydroxide and 200 g of sodium chloride are added and vigorously thoroughly stirred until all salts have dissolved. Then, 1000 ml of ethyl acetate is added and vigorously thoroughly stirred again. The organic phase is separated, and the aqueous phase is then re-extracted twice with a mixture that consists of 500 ml of THF/500 ml of ethyl acetate in each case. The combined organic phases are concentrated by evaporation in a vacuum, and the remaining oil is dissolved in 2500 ml of methanol. 180 ml of concentrated hydrochloric acid is added, and it is stirred for two hours at room temperature. Then, 3000 ml of methyl-tert-butyl ether is added, and it is cooled to 0° C. (in this case, the title compound completely crystallizes out). The crystals are filtered off and rewashed twice with a mixture that consists of cold methanol/methyl-tert-butyl ether 1:1. The crystals are dried for 8 hours at 40° C. in a vacuum.

Yield: 544.1 g of colorless crystals (81% of theory relative to the (S)-Z-serine methyl ester that is used)

Elementary Analysis:

| | | | | |
|---|---|---|---|---|
| Cld. | C 45.89 | H 6.81 | N 12.35 | Cl 20.84 |
| Fnd. | C 46.12 | H 7.02 | N 12.22 | Cl 20.71 |

Cleavage of the Z Protective Group by Hydrogenation 1b) 3-Aza-5-amino-1-(R)-hydroxymethyl-1-amino-pentane, trihydrochloride 544.0 g (1599 mmol) of the title compound of Example 1a is dissolved in a mixture that consists of 4400 ml of methanol/1100 ml of water and 55 ml of concentrated hydrochloric acid, and it is hydrated over 8 g of hydrating catalyst Pd/C (10% Pd) at room temperature (6 bar). The catalyst is filtered off, and the filtrate is concentrated by evaporation in a vacuum as much as possible. The remaining oil is taken up with 950 ml of concentrated hydrochloric acid and stirred at room temperature (in this case, crystallization already sets in). Then, a mixture that consists of 2500 ml of ethanol/750 ml of n-butanol is carefully added in drops (in this case, the product crystallizes out). It is cooled to 0° C. and stirred for 3 hours at this temperature, the precipitated crystlals are filtered out, and it is rewashed twice with a mixture that consists of cold ethanol/n-butanol=3:1. Then, the crystals are dried in a vacuum at 50° C. (7 hours).

Yield: 360.7 g of colorless crystals (93% of theory)
Elementary Analysis:

| Cld. | C 24.76 | H 7.48 | N 17.32 | Cl 43.85 |
|------|---------|--------|---------|----------|
| Fnd. | C 24.59 | H 7.61 | N 17.14 | Cl 43.62 |

Total yield over all stages: 75% of theory

Example 2

Z Method/One-Pot Process

3-Aza-5-amino-1-(R)-hydroxymethyl-1-amino-pentane, trihydrochloride

Analogously to what is described in Example 4, the Z intermediate compounds are converted in a single-pot variant into the target compound.

The cleavage of the Z protective group is carried out by acid hydrolysis with HCl.

To this end, intermediate compound IIIa is dissolved in concentrated hydrochloric acid and heated for 6 hours to 90° C. It is cooled to room temperature. Then, a mixture that consists of ethanol/n-butanol (3:1) is carefully added in drops (in this case, the product crystallizes out). It is cooled to 0° C. and stirred for 3 hours at this temperature, the precipitated crystals are filtered off, and it is rewashed twice with a mixture that consists of cold ethanol/n-butanol=3:1. Then, the crystals are dried in a vacuum at 50° C. (7 hours).

Yield: Colorless crystals (91% of theory)
Elementary Analysis:

| Cld. | C 24.76 | H 7.48 | N 17.32 | Cl 43.85 |
|------|---------|--------|---------|----------|
| Fnd. | C 24.53 | H 7.71 | N 17.17 | Cl 43.59 |

Total yield over all stages: 73% of theory

Example 3

Boc Method/Two-Pot Process

3-Aza-5-amino-1-(R)-hydroxymethyl-1-amino-pentane, trihydrochloride

Analogously to what is described in Example 1, the Boc intermediate compounds are converted in a two-pot process (with intermediate isolation of IIb) into the target compound.
Elementary Analysis:

| Cld. | C 24.76 | H 7.48 | N 17.32 | Cl 43.85 |
|------|---------|--------|---------|----------|
| Fnd. | C 24.50 | H 7.67 | N 17.13 | Cl 43.64 |

Total yield over all stages: 71% of theory

Example 4

Boc Method/Single-Pot Process

3-Aza-5-amino-1-(R)-hydroxymethyl-1-amino-pentane, trihydrochloride 433 g (1974.2 mmol) of (S)-Boc-serine methyl ester is introduced into 2000 ml of tetrahydrofuran (THF) and 199.3 g (2369 mmol) of dihydropyran, and 100 mg of p-toluenesulfonic acid is added. It is heated for 6 hours at 60° C. After the reaction is completed, 1000 ml of solvent is distilled off (removal of excess dihydropyran).

2000 ml of fresh THF is added, and 227 g (6.00 mol) of sodium borohydride is added, and it is cooled to 0° C. 2500 ml of methanol is slowly added in drops to this suspension, and the temperature is kept between 2° C. and 6° C. (gas generation). After the addition is completed, it is stirred for 3 more hours at 10° C. 4000 ml of water is added, and the organic solvent is distilled off to a large extent in a vacuum. Then, it is extracted twice with 2000 ml of ethyl acetate in each case. The combined ethyl acetate phases are largely concentrated by evaporation in a vacuum, and the remaining oil is taken up in 3000 ml of THF.

405 g (4.00 mol) of triethylamine is added and cooled to −5° C. Then, 248.7 g (2.17 mol) of methanesulfonic acid chloride is added in drops, and the temperature is kept between −5° C. to 0° C. After the addition is completed, it is stirred for one more hour at 0° C.

1923 g (32 mol) of 1,2-diaminoethane is quickly added to the thus obtained solution, and it is stirred for 5 hours at 50° C. 6000 ml of water, as well as 176 g (4.4 mol) of sodium hydroxide and 200 g of sodium chloride are added and vigorously thoroughly stirred until all salts are dissolved. Then, 1000 ml of ethyl acetate is added, and it is vigorously thoroughly stirred again. The organic phase is separated, and the aqueous phase is then re-extracted twice with a mixture that consists of 500 ml of THF/500 ml of ethyl acetate in each case. The combined organic phases are concentrated by evaporation in a vacuum.

The remaining oil is dissolved in 1400 ml of concentrated hydrochloric acid, and it is heated for 6 hours to 90° C. It is cooled off to room temperature. Then, a mixture that consists of 3150 ml of ethanol/1050 ml of n-butanol is carefully added in drops (in this case, the product crystallizes out). It is cooled to 0° C. and stirred for 3 hours at this temperature, the precipitated crystals are filtered out, and it is rewashed twice with a mixture that consists of cold ethanol/n-butanol=3:1. Then, the crystals are dried in a vacuum at 50° C. (7 hours).

Total yield: 398 g of colorless crystals (72% of theory over all stages)

Elementary Analysis:

| Cld. | C 24.76 | H 7.48 | N 17.32 | Cl 43.85 |
|---|---|---|---|---|
| Fnd. | C 24.51 | H 7.65 | N 17.49 | Cl 43.70 |

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosures of all applications, patents and publications, cited herein and of corresponding German application No. 10 2004 026 102.4, filed May 25, 2004 and U.S. Provisional Application Ser. No. 60/575,838, filed Jun. 2, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the production of 1-hydroxymethyl-1,3,5-triazapentane (I) or a salt thereof,

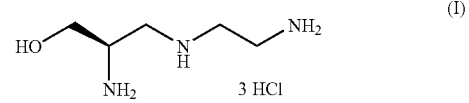
(I)

comprising reacting a compounds of formula IVa or IVb

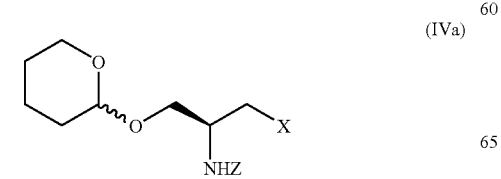
(IVa)

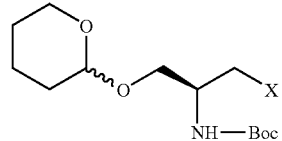
(IVb)

wherein X is an —OSO$_2$Me or p-toluenesulfoxy group, with 1,2-diaminoethane to form an amines of formula IIIa or IIIb,

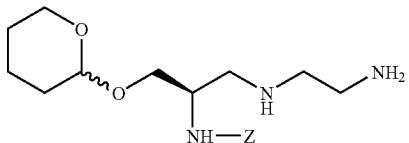
(IIIa)

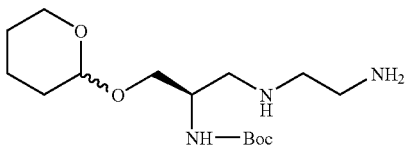
(IIIb)

cleaving the THP-protective group to obtain compound IIa or IIb or a salt thereof,

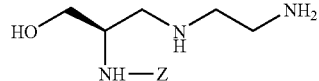
(IIa)

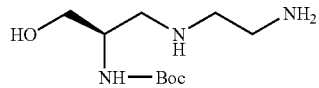
(IIb)

and further cleaving the protective groups located on the nitrogen atom.

2. A process for the production of 1-hydroxymethyl-1,3,5-triazapentane (I) or a salt thereof,

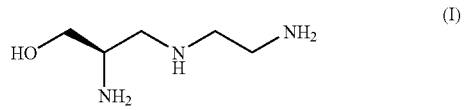
(I)

comprising reacting a compound of formulas IVa or IVb

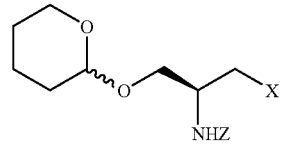
(IVa)

-continued

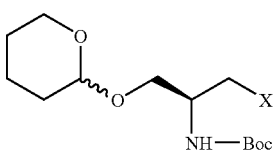
(IVa)

wherein X is an —OSO₂Me or p-toluenesulfoxy group, with 1,2-diaminoethane to form an amines of formula IIIa or IIIb

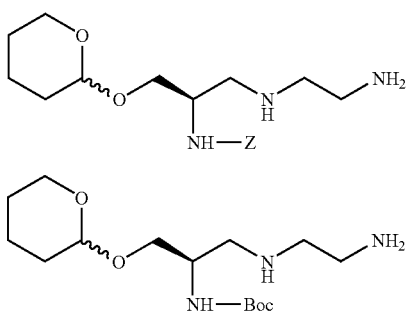
(IIIa)
(IIIb)

and cleaving the protective groups in a single-pot process.

3. The process for the production of the compound of formula I, according to claim 1

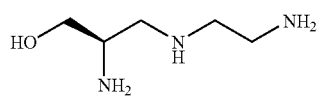
(I)

wherein stages IIa, IIIa and IVa are passed through.

4. A compound of formula IIa or a salt thereof

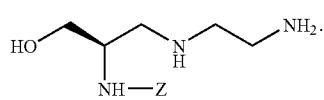
(IIa)

5. A compound of formula IIb or a salt thereof

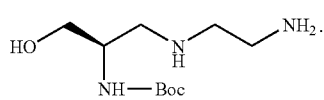
(IIb)

6. A compound of formula IIIa

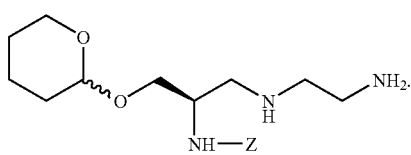
(IIIa)

7. A compound of formula IIIb

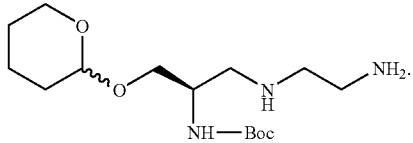
(IIIb)

8. The process according to claim 1, wherein a corresponding enantiomers of IVa or IVb is used in the synthesis sequence.

9. The process according to claim 1, wherein a corresponding racemates of IVa or IVb is used in the synthesis sequence.

10. The process according to claim 1 wherein said reaction of a compound IVa or IVb with 1,2-diaminoethane is carried out at a temperature of 10 to 70° C. for a reaction time of 3 to 12 hr.

11. The process according to claim 2 wherein said reaction of a compound IVa or IVb with 1,2-diaminoethane is carried out at a temperature of 10 to 70° C. for a reaction time of 3 to 12 hr.

12. The process according to claim 1 wherein the protecting group is cleaved by treatment with aqueous hydrochloric acid.

13. The process according to claim 2 wherein the protecting group is cleaved by treatment with aqueous hydrochloric acid.

14. The process according to claim 1 wherein compounds comprising the protective group Z are used.

15. The process according to claim 2 wherein compounds comprising the protective group Z are used.

16. The process according to claim 1 wherein said salt of the compound of formula I is a hydrochloride, hydrobromide, sulfate, or hydrosulfate.

17. The process according to claim 2 wherein said salt of the compound of formula I is a hydrochloride, hydrobromide, sulfate, or hydrosulfate.

18. A compound of formula I or a salt thereof

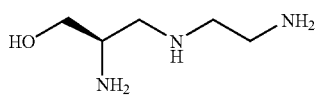
(I)

produced by a process according to claim 1.

19. A compound of formula I or a salt thereof

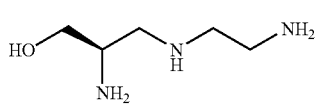
(I)

produced by a process according to claim 2.

20. The process according to claim 2, wherein a corresponding enantiomer of IVa or IVb is used in the synthesis sequence.

21. The process according to claim 2, wherein a corresponding racemate of IVa or IVb is used in the synthesis sequence.

* * * * *